(12) United States Patent
Hijikata et al.

(10) Patent No.: US 9,133,847 B2
(45) Date of Patent: Sep. 15, 2015

(54) DISPOSABLE MAGNETICALLY-LEVITATED CENTRIFUGAL PUMP

(75) Inventors: Wataru Hijikata, Yokohama (JP);
Tadahiko Shinshi, Yokohama (JP);
Setsuo Takatani, Tokyo (JP)

(73) Assignees: Tokyo Institute of Technology, Tokyo (JP); Tokyo Medical and Dental University, Tokyo (JP)

( * ) Notice: Subject to any disclaimer, the term of this patent is extended or adjusted under 35 U.S.C. 154(b) by 266 days.

(21) Appl. No.: 13/392,879

(22) PCT Filed: Aug. 27, 2010

(86) PCT No.: PCT/JP2010/005289
§ 371 (c)(1),
(2), (4) Date: Feb. 28, 2012

(87) PCT Pub. No.: WO2011/024470
PCT Pub. Date: Mar. 3, 2011

(65) Prior Publication Data
US 2012/0156071 A1    Jun. 21, 2012

(30) Foreign Application Priority Data

Aug. 28, 2009 (JP) .................................. 2009-197785

(51) Int. Cl.
*F04D 29/048* (2006.01)
*F04D 1/00* (2006.01)
(Continued)

(52) U.S. Cl.
CPC ........... *F04D 13/027* (2013.01); *A61M 1/1015* (2014.02); *A61M 1/1031* (2014.02); *F04D 1/00* (2013.01); *F04D 13/025* (2013.01); *F04D 13/026* (2013.01); *F04D 13/064* (2013.01); *F04D 13/0633* (2013.01); *F04D 29/048* (2013.01); *F04D 29/605* (2013.01);
(Continued)

(58) Field of Classification Search
CPC ............... F04D 7/00; F04D 7/02; F04D 1/00;
F04D 13/024; F04D 13/025; F04D 13/026;
F04D 13/027; F04D 25/0256; F04D 29/048;
F04D 29/058; F04D 29/605
USPC ............................ 417/63, 420, 410.1; 415/90
See application file for complete search history.

(56) References Cited

U.S. PATENT DOCUMENTS 5,658,136 A * 8/1997 Mendler ........................ 417/420
5,947,703 A * 9/1999 Nojiri et al. ................... 417/420
(Continued)

FOREIGN PATENT DOCUMENTS

EP     1 932 552      *  6/2008  .............. A61M 1/10
EP     1932552   A1  *  6/2008
(Continued)

OTHER PUBLICATIONS

International Search Report for PCT/JP2010/005289 from the Japanese Patent Office completed on Jan. 21, 2011 and mailed Feb. 1, 2011 (3 pages).
(Continued)

*Primary Examiner* — Bryan Lettman
*Assistant Examiner* — Timothy P Solak
(74) *Attorney, Agent, or Firm* — Pyprus Pte Ltd

(57) ABSTRACT

A magnetically-levitated centrifugal pump comprises a pump head section and a pump section, where the pump section comprises a stator, a torque transmission disc, a motor, a displacement sensor, and a pump housing.

4 Claims, 13 Drawing Sheets

(51) Int. Cl.
  *F04D 13/02* (2006.01)
  *F04D 29/60* (2006.01)
  *F04D 29/62* (2006.01)
  *H02K 49/10* (2006.01)
  *H02N 15/00* (2006.01)
  *F04D 13/06* (2006.01)
  *F16C 32/04* (2006.01)
  *A61M 1/10* (2006.01)
  *H02K 7/09* (2006.01)

(52) U.S. Cl.
  CPC ............ F04D29/628 (2013.01); F16C 32/048 (2013.01); F16C 32/0465 (2013.01); F16C 32/0468 (2013.01); H02K 49/106 (2013.01); H02N 15/00 (2013.01); A61M 1/101 (2013.01); F16C 32/0497 (2013.01); H02K 7/09 (2013.01)

(56) References Cited

U.S. PATENT DOCUMENTS

| | | | |
|---|---|---|---|
| 6,737,777 B2* | 5/2004 | Werfel et al. | 310/90.5 |
| 2006/0222533 A1* | 10/2006 | Reeves et al. | 417/420 |
| 2010/0040491 A1* | 2/2010 | Shinshi et al. | 417/420 |

FOREIGN PATENT DOCUMENTS

| | | |
|---|---|---|
| JP | 3-286775 A | 12/1991 |
| JP | WO2007029623 A1 | 3/2007 |
| JP | 2009106690 A | 5/2009 |

OTHER PUBLICATIONS

Centrifugal pump without bearings or seals, World Pumps, Jul. 2002.
CentriMag Left Ventricular Assist System, J Cardiovasc Surg (Torino) 2007.
Magnetically Suspended Centrifugal Blood Pump With a Radial Magnetic Driver, ASIO Journal, 2005, P60-64.

* cited by examiner

DISPOSABLE MAGNETICALLY-LEVITATED CENTRIFUGAL PUMP

TECHNICAL FIELD

The present invention relates to a magnetically-levitated centrifugal pump which has a disposable impeller section, similar to an extracorporeal magnetically-levitated blood pump and a canned pump.

BACKGROUND ART

For long term cardiopulmonary support equipment such as long-term PCPS or ECMO, centrifugal blood pumps that can be used for two weeks to one month are presently demanded. The centrifugal pump that use magnetically-levitated technology for the bearings that supports an impeller has been partly sold and developed in order to enhance durability of bearings section and to reduce bloodclot formation and haemolysis (e.g., referred to WO 2007/029623 A1; Hoshi et al., Magnetically Suspended Blood Pump with a Radial Magnetic Driver, ASIO journal, pp. 60-64, (2005)). In order to achieve sufficient stiffness of the magnetic bearing, high performance magnets such as neodymium magnets are used at a disposable impeller section in all of these pumps. Neodymium magnets are also used at disposable centrifugal pump using many mechanical bearings in order to generate magnetic coupling to transmit torque from a motor to an impeller.

PRIOR ART DOCUMENTS

Patent Documents

Patent Document 1: WO 2007/029623 A1

Non-Patent Documents

Non-patent Document 1: Rete Schob, Centrifugal pump without bearings or seals, World Pumps, July 2002.
Non-patent Document 2: CentriMag Left Ventricular Assist System Catalogue, Levi tronix.
Non-patent Document 3: H. Hoshi, K. Kataoka, K. Ohuchi, J. Asama, Shinshi, A. Shimokohbe and S. Takatani, Magnetically Suspended Blood Pump with a Radial Magnetic Driver, AS10 journal, pp. 60-64, (2005).

SUMMARY OF THE INVENTION

The Problem to be Solved by the Invention

Since neodymium which is a main ingredient of the permanent magnets are only produced in China and these permanent magnets are expensive, the supply of rare-metal-containing products could be easily controlled by the domestic strategies of the Country. Furthermore, it is difficult to form the impeller to be integral by embedding neodymium having low demagnetization temperature owing to injection resin temperature when the impeller is formed by injection molding.

In addition, although it is disclosed in FIG. 8 of WO 2007/029623 A1 (the patent reference 1), which is depicted as FIG. 13 herein, that only magnetic materials are used for a rotor, there is a problem in this configuration that fabrication is difficult because small fan-shaped magnets are arranged on periphery of a torque transmission disc. There is another problem that the magnetically-levitated blood pump in FIG. 8 of the patent reference 1, in which only magnetic materials are used for the rotor, has low rigidity to support the impeller, compared to the one that the permanent magnets are used for the rotor.

There is another problem that the magnetically-levitated blood pump in FIG. 8 of the patent reference 1, in which only magnetic materials are used for the rotor, has low rigidity to support the impeller, compared to the one that the permanent magnets are used for the rotor.

The present invention is to solve these problems and to provide a magnetically-levitated centrifugal pump that does not use the permanent magnets for disposable sections.

Means for Solving the Problems

The disposable magnetically-levitated centrifugal pump according to the present invention comprises a pump head section and a pump section.

The pump head section comprises a cylindrical rotor, an impeller, and a pump head housing. The cylindrical rotor is made from magnetic material and has protrusions at upper part and at lower part of internal circumference surface of the ring-shaped rotor body. The protrusions have a specified or predetermined width and protrude inward or toward inside direction of the ring-shaped rotor body. The impeller is forced to be rotated along with the rotation of the rotor. The pump head housing has a fluid inlet, a fluid outlet and a space section that is arranged so as to enable free rotation of the impeller. The pump head housing further has a rotor accommodation section, which is arranged so as to enable rotation of the rotor by magnetic force, which protrude from the bottom of the space section.

The pump section comprises a stator, a torque transmission disc, a motor, a displacement sensor, and a pump housing. The stator has a rotor insertion section, on the side of one end section. The rotor insertion section has depth longer or deeper than protrusion length of a rotor accommodation section and is disposed so as to be able to insert and remove the rotor accommodation section. The stator has at least three electromagnets for magnetic bearing at regular intervals. The at least three electromagnets magnetically couple with the rotor.

The torque transmission disc which is formed by bonding ring components between a plurality of ring-shaped permanent magnets and placing another ring component on top of the uppermost ring-shaped permanent magnet. The ring components are made from magnetic material and comprise protrusion sections at positions facing the protrusions of the rotor. The pluralities of ring-shaped permanent magnets are magnetized in the thickness direction thereof. The like-poles of one of the ring-shaped permanent magnets and one of the ring components, which is next to the ring-shaped permanent magnet, face each other. The torque transmission disc is disposed inside the rotor insertion section and is configured to magnetically couple with the rotor.

The motor is connected to a rotating shaft going through from the other end side of the stator to the one end side and rotationally drives the torque transmission disc through the rotating shaft. The displacement sensor is disposed on the stator and measures displacement in radial directions of the rotor. The pump housing has the stator, the torque transmission disc, the motor, and the displacement sensor. The pump housing can accommodate the pump head section in a manner that the pump head section is inserted to the housing and removed from the housing.

The stator further has an electro-magnet core. The electro-magnet core has a bottom plate section, in which a shaft hole going through the rotating shaft is provided at the center, a mounting section which rises parallel to and in the same direction as the shall hole from an end point of the bottom plate section, and protrusion sections which protrude towards the central axis of the shaft hole on the upper part side of the mounting section. The electromagnet for magnet bearing is formed by winding a coil around the electro-magnet core.

The torque transmission disc is fixed on the rotating shall so that plural ring-shaped permanent magnets are disposed at position against the rotor in the rotor insertion section and at position that ranges from the protrusion sections to the bottom plate section.

The disposable magnetically-levitated centrifugal pump according to the present invention is integrated with the rotor and the impeller by injection molding.

Technical Effect of the Invention

In the present invention, disposable sections can be produced inexpensively because the rotor only has magnetic materials and does not have permanent magnets.

Furthermore, because the rotor has simple structure in which pole-face is formed on internal circumference of the ring-shaped components by fluting, processing accuracy is improved and inexpensive fabrication becomes possible.

Still further, because the rotor does not have the permanent magnets, heat generated during manufacturing does not become a problem, and then fabrication using injection molding and others becomes possible and the fabrication can be made at low cost.

DESCRIPTION OF EMBODIMENTS

Embodiments of the present invention are described as follows, based on the drawings.

FIG. 1 to FIG. 12 show an embodiment that the disposable magnetically-levitated centrifugal pump according to the present invention is applied to a disposable magnetically-levitated centrifugal pump 1.

Figure 1:
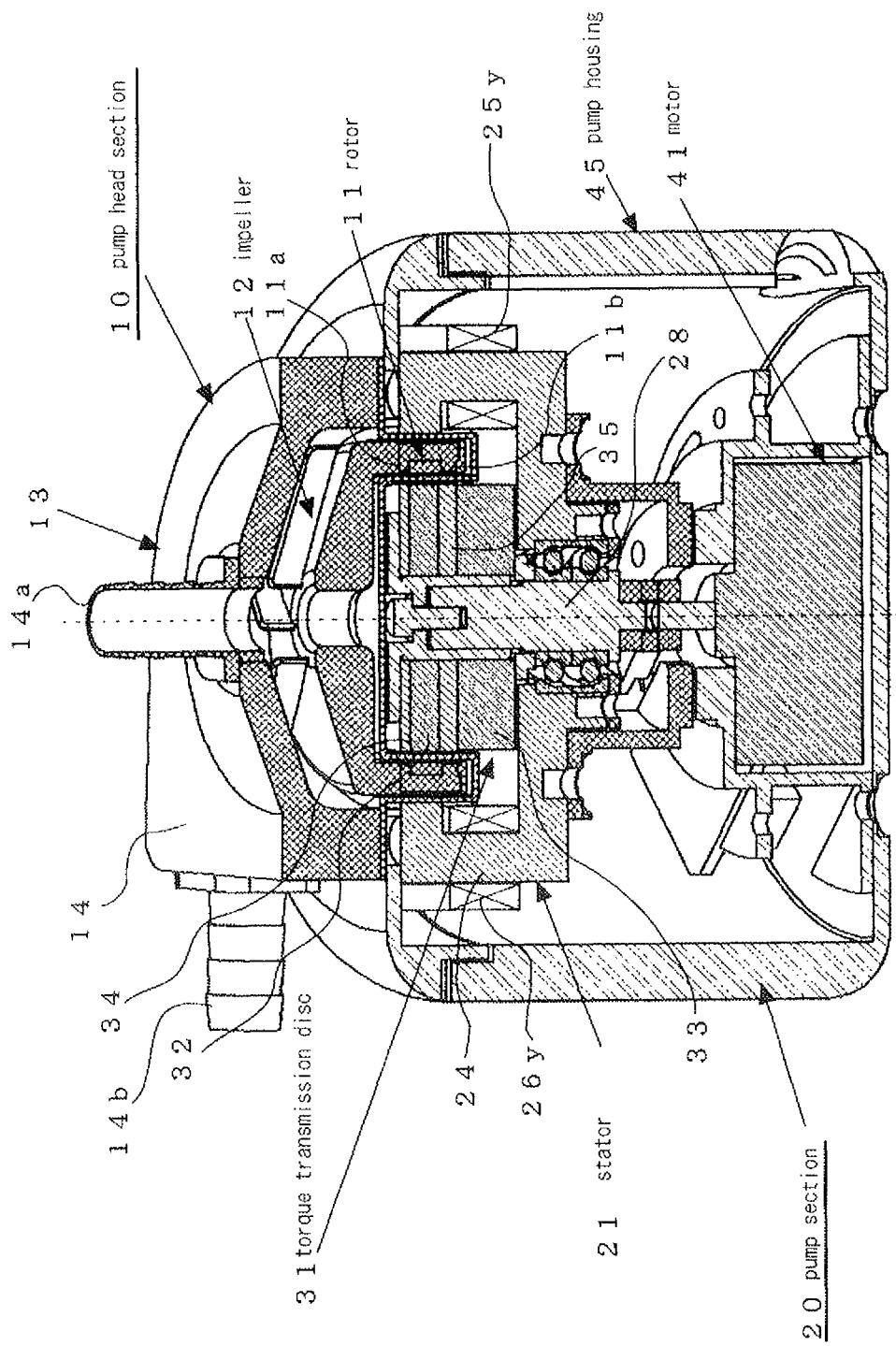
FIG. 1 is a sectional drawing showing an embodiment in which the disposable magnetically-levitated centrifugal pump according to the present invention is applied to a disposable magnetically-levitated centrifugal pump 1.
Figure 2:
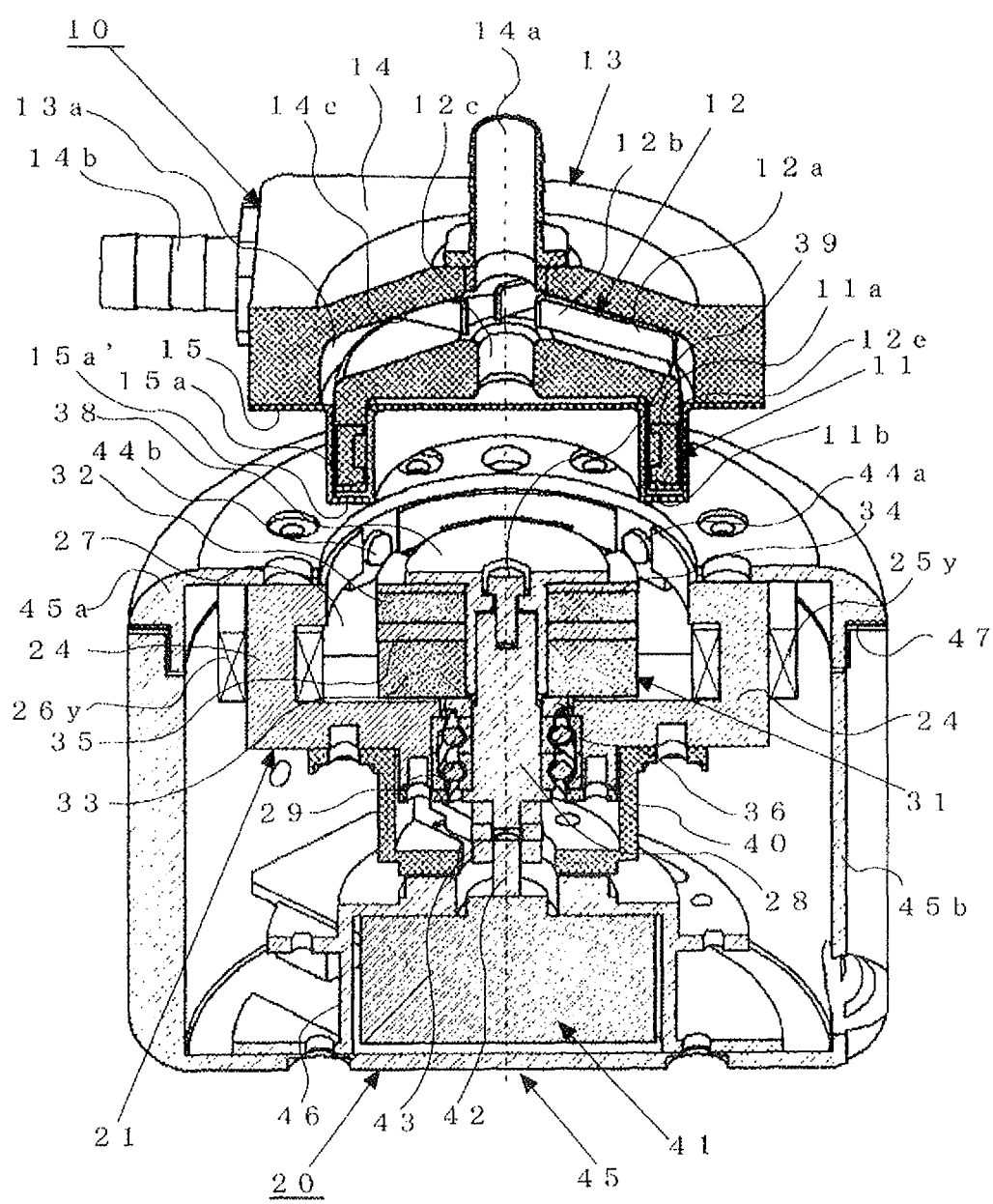
FIG. 2 is a sectional drawing showing a state that the pump head section 10 of FIG. 1 is separated from the pump section 20.
Figure 3:
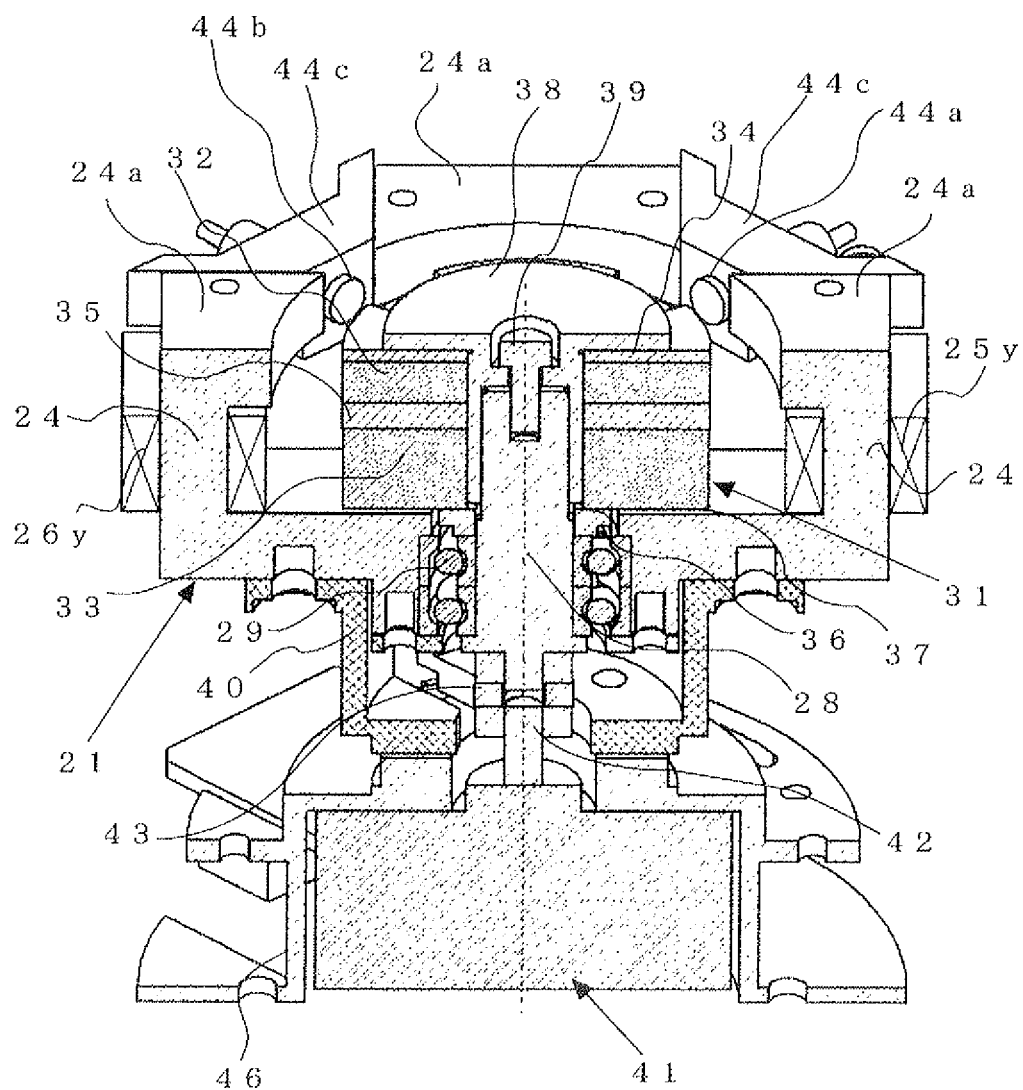
FIG. 3 is a sectional drawing showing an essential part of the pump section 20 of FIG. 1.

As shown in FIG. 1 to FIG. 3, the disposable magnetically-levitated centrifugal pump 1 according to the present embodiment comprises a disposable pump head section 10, a reusable pump section 20 which this pump head section 10 can be inserted to and removed from, and a control equipment 50.

At first, the pump head section 10 will be described.

The pump head section 10, for example, comprises a ring-shaped rotor 11 consisting of magnetic material such as electromagnetic soft iron, an impeller 12 that is integrated with the rotor 11, and a pump head housing 13 accommodating the rotor 11 and the impeller 12.

The rotor 11 comprises a ring which has a U-shaped sectional schematic view, in which protrusion sections 11b and 11c with a specified width, which protrude towards the inside on upper and lower parts of internal circumference surface of main body of a ring-shaped rotor 11a, are made by tooth-space forming or tooth-grave forming. Here, the main body of the rotor 11a constitutes a pole-face 100, the protrusion section 11b constitutes a pole-face 101, the protrusion section 11c constitutes a pole-face 102. The protrusion sections 11b and 11c which constitute the pole-faces 101 and 102 are provided to transmit motor torque to the rotor 11 through pole-faces 103 and 104 of the torque transmission disc 31 mentioned below.

The impeller 12 comprises an impeller body 12a connected on a top end surface of the rotor 11, a plurality of wings 12b provided at a specified interval to push blood toward the impeller body 12a, and a wash out hole 12c provided by making a hole at the center of the impeller body 12 in its axis direction. The impeller 12 is made, for example, from lightweight synthetic resin material such as acryl resin. In the present embodiment, injection molding is performed to integrate the rotor 11 and the impeller 12. Then, an external diameter of the impeller main body 12a equals to an external diameter of the rotor 11, and in a junction 12d between the impeller main body 12a and the rotor 11 a cylindrical rising section 12e whose shape is equal to the shape of the top end surface of the rotor 11 is formed.

A pump head housing 13 is constructed by integrating the first housing 14 having cup shape and the second housing 15 which is disposed on the opening side of the first housing 14 to blockade the opening side of the first housing 14 by gluing them together with adhesives and others. The pump head housing 13 is made, for example, from lightweight synthetic resin material such as acryl resin, similar to the impeller 12.

The first housing 14 has a blood flow inlet 14a at the top section, a blood flow outlet 14b in the lateral face or on the side lace, and a concave section 14c which forms a space section 13a to dispose the impeller 12 to rotate freely.

The second housing 15 has a cylindrical rotor accommodation section 15a, which disposes the rotor 11 to rotate it with magnetic force, on the opposite side of the facing surface of the concavity 14c of the first housing 14 to protrude into the opposite side to the first housing 14.

In the present embodiment, similar to the patent document 1 (WO 2007/029623 A1), height dimension from a bottom section 15a' of a rotor accommodation section 15a of the pump head housing 13 to upper part of the impeller 12 is set to be 39.5 mm, height of the rotor 11 is set to be 10 mm, an external diameters of the impeller 12 and the rotor 11 are set to be 50 mm, and an external diameter of the rotor accommodation section 15a of the pump head housing 13 is set to be 53 mm.

Then, a pump section 20 will be described.

The pump section 20, for example, comprises a stator 21 a motor 41 the first displacement sensor 44a, the second displacement sensor 44b and a pump housing 45. The stator 21 is for example made from magnetic material such as electromagnetic soft iron and disposes electro-magnets 25x, 26x, 25y, and 26y for magnet bearings causing magnetic coupling to the rotor 11. The torque transmission disc 31 causes magnetic coupling with or toward the rotor 11. The motor 41 rotationally drives the torque transmission disc 31. The first displacement sensor 44a and the second displacement sensor 44b measure displacement in radial directions of the rotor 11. The pump housing 45 mounts the stator 21, the torque transmission disc 31, the motor 41, the first displacement sensor 44a, and the second displacement sensor 44b.

The stator 21 comprises a cross-shaped bottom plate section 22 that is provided with a shaft hole 23 at its center, through which a rotating shaft 28 installing the torque transmission disc 31 as mentioned later goes, a mounting section 24b rising parallel to and in the same direction as the shaft hole 23 from each of the top end points of this bottom plate section 22, and an electro-magnet core 24 having protrusion sections 24a protruding toward the central axis of the shaft hole 23 in each top edge side of the mounting sections 24b.

The shaft hole 23 is provided with a cylindrical section 23a protruding into the bottom side of the bottom plate section 22 in the opposite direction from the mounting section 24b. Bearings 29 are mounted within the cylindrical section 23a so that it is constituted to axially support the rotating shaft 28 to rotate freely.

An electro-magnet core 24 comprises electromagnetic soft iron core using pure iron or electromagnetic soft iron core made by forming powder core by compressing fine grains of pure iron and then by gluing them with adhesives, a coil is winded around this electromagnetic soft iron core, and four electro-magnets 25x, 26x, 25y, and 26y for magnet bearings are arranged at every 90 degrees. These electro-magnets 25x, 26x, 25y, and 26y and the rotor 11 constitutes a magnet bearings 30 supporting a load of the impeller 12 by magnetic force without contact. In other words, protrusion sections 24a having pole-faces 105x and 106x for X direction control are disposed on the opposite side of the rotor 11 in the X direction to each other, the protrusion sections 24a having pole-faces 105y and 106y for Y direction control is disposed on the opposite side of the rotor 11 in the Y direction to each other. In addition, mounting sections 24b are disposed at lower position of each of the protrusion sections 24a to be able to wind up more coils. Note that because power supply to the four electro-magnets 25x, 26x, 25y, and 26y for magnet bearings is performed by usual method, its explanation is omitted.

Here, the length of the bottom plate section 22 of the electro-magnet core 24 is set to be 82 mm, height from under surface of the bottom plate section 22 of the electro-magnet core 24 to the protrusion sections 24a of the electro-magnet core 24 is set to be 28 mm.

The respective four electro magnets 25x, 26x, 25y, and 26y for magnet bearings constitute pole-faces 105x, 106x, 105y, and 106y by the protrusion sections 24a protruding towards the central axis of the shaft hole 23. Then, the pole-faces 105x, 106x, 105y, and 106y are along the sub-region of the pole-face 100 of the rotor 11, gaps in dimension between them are set to be narrow. In addition, a rotor insertion section 27 that is provided with a rotor accommodation section 15a of the pump head housing 13 so as to be able to be inserted and removed is formed by the pole-faces 105x, 106x, 105y, and 106y that are respectively formed with the four electro-magnets 25x, 26x, 25y, and 26y for magnet bearings. Here, the depth from a top edge of the protrusion sections 24a forming the rotor insertion section 27 to the bottom plate section 22 is greater than protrusion length of the rotor accommodation section 15a.

The torque transmission disc 31 is installed on the internal circumference side of the rotor 11 and on the upper part of the bottom plate section 22 of the electro-magnet core 24. This torque transmission disc 31 has a structure in which e.g. a ring-shaped component 34 consisting of magnetic material such as electromagnetic soft iron, e.g., a permanent magnet 32 such as neodymium, e.g., a ring-shaped component 35 consisting of the magnetic material such as electromagnetic soft iron, and e.g., a permanent magnet 33 such as neodymium, are in turn piled from the top. Tooth space forming is performed so that similar protrusions 34a and 35a are disposed at positions opposing to the protrusions 11b and 11c of the rotor 11, in each of the ring-shaped components 34 and 35. Specifically, a pole-face 103 by a protrusion 34a and a pole-face 101 by a protrusion 11b of the rotor 11 face each other, and a pole-face 104 by a protrusion 35a and a protrusion 11c of the rotor 11 face each other.

A permanent magnet 32 and a permanent magnet 33 are magnetized in a thrust (Z) direction, the magnetized directions may face each other or be the same as each other. As explained with an example in FIG. 5, a magnetic flux 111 going out from the N pole of the permanent magnet 32 produces a steady magnetic flux constituting a closed loop of the magnetic flux 111 by returning to the S pole of the permanent magnet 32 through the ring component 35→the pole face 104→a gap→the pole face 102→the rotor 11→the pole face 101→a gap→the pole face 103→ the ring component 34. Similarly, the magnetic flux 112 going out from the N pole of the permanent magnet 33 produces a steady magnetic flux constituting a closed loop of the magnetic flux 112 by returning to the S pole of the permanent magnet 33 through the ring component 35→the pole face 104→a gap→the pole face 102→the rotor 11→the pole face 100→a gap→the pole face 105y→the stator 21→a gap.

Here, the reason why the protrusions 34a, 35a, 11b, and 11c are equipped in the rotor 11 and the torque transmission disc 31 will be described.

Figure 4:
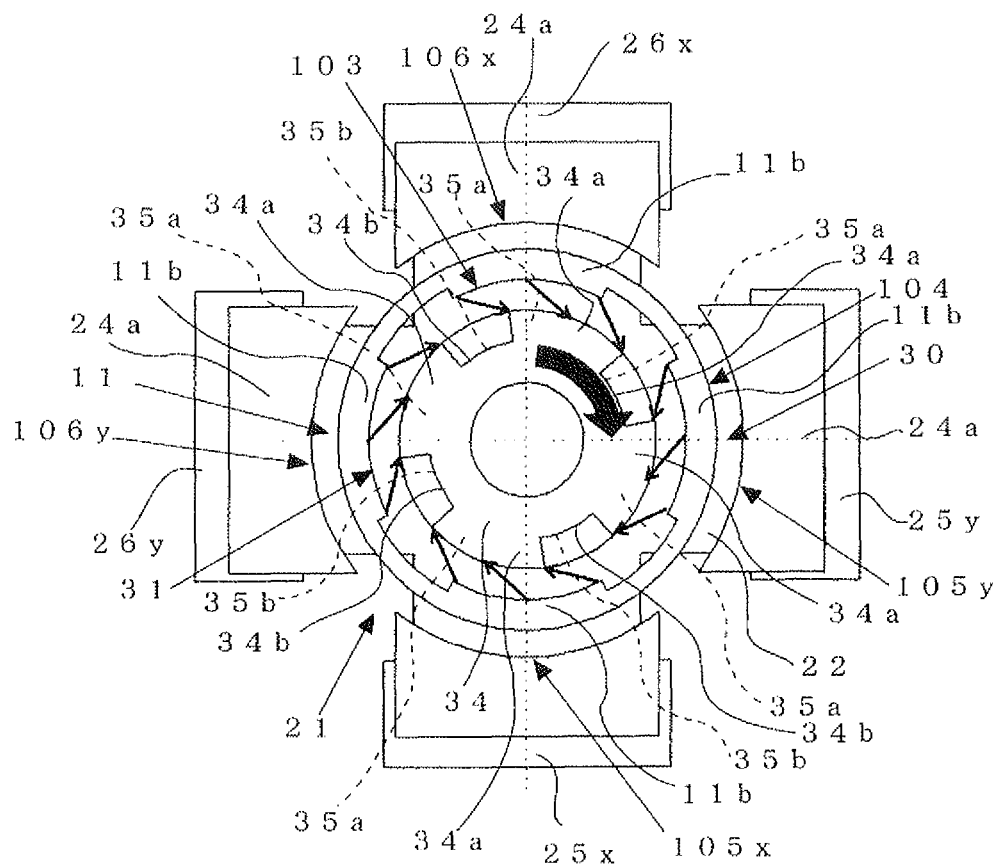
FIG. 4 is an explanation drawing that indicates the magnet bearings 30 of FIG. 1 in plan view.
Figure 4:
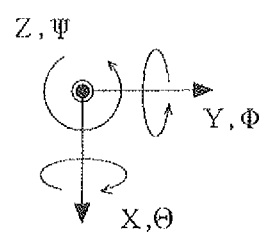

As shown in FIG. 4, misalignment occurs in the protrusions 34a, 35a, 11b, and 11c when rotating the torque transmission disc 31. Because torque (propagation torque) undoing this misalignment of the protrusions 34a, 35a, 11b, and 11c occurs in the rotor 11 by the magnetic flux 111 of the two permanent magnets 32 and 33, and, as a result, motor torque rotating the torque transmission disc 31 is transmitted to the rotor 11.

Because the misalignment as shown in FIG. 4 cannot be made if one of the protrusions 34a and 35a or one of the protrusions 11b and 11c does not exist, the protrusions 34a, 35a, 11b, and 11c are necessary for both the torque transmission disc 31 and the rotor 11 to transmit the motor torque.

Next, ditches 34b and 35b forming the protrusions 34a and 35a of the torque transmission disc 31 will be described.

Figure 9:
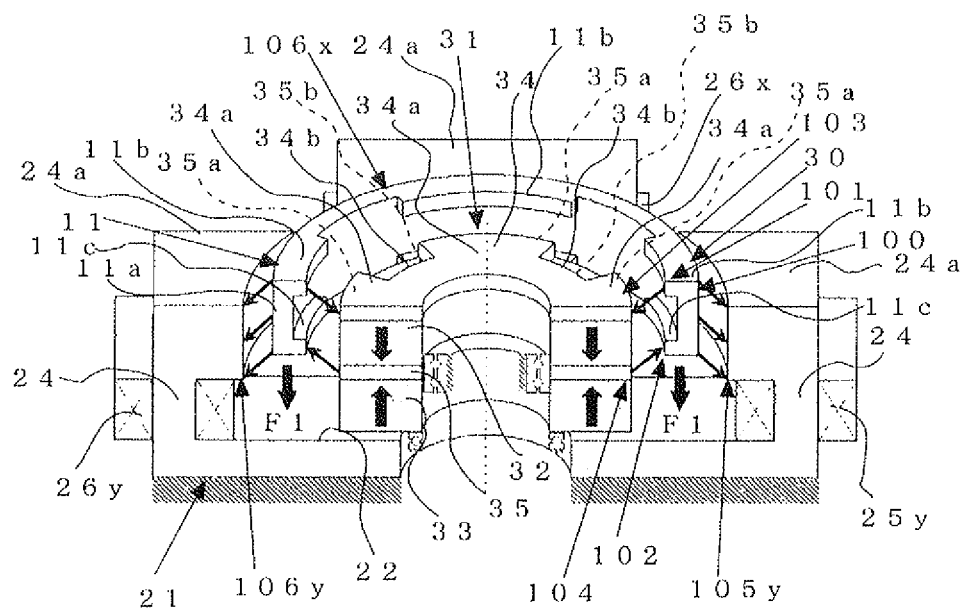
FIG. 9 is an explanation drawing showing restoring force F1 in the magnet bearings 30 of FIG. 1.
Figure 9:
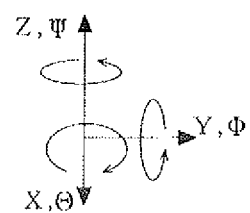
Figure 10:
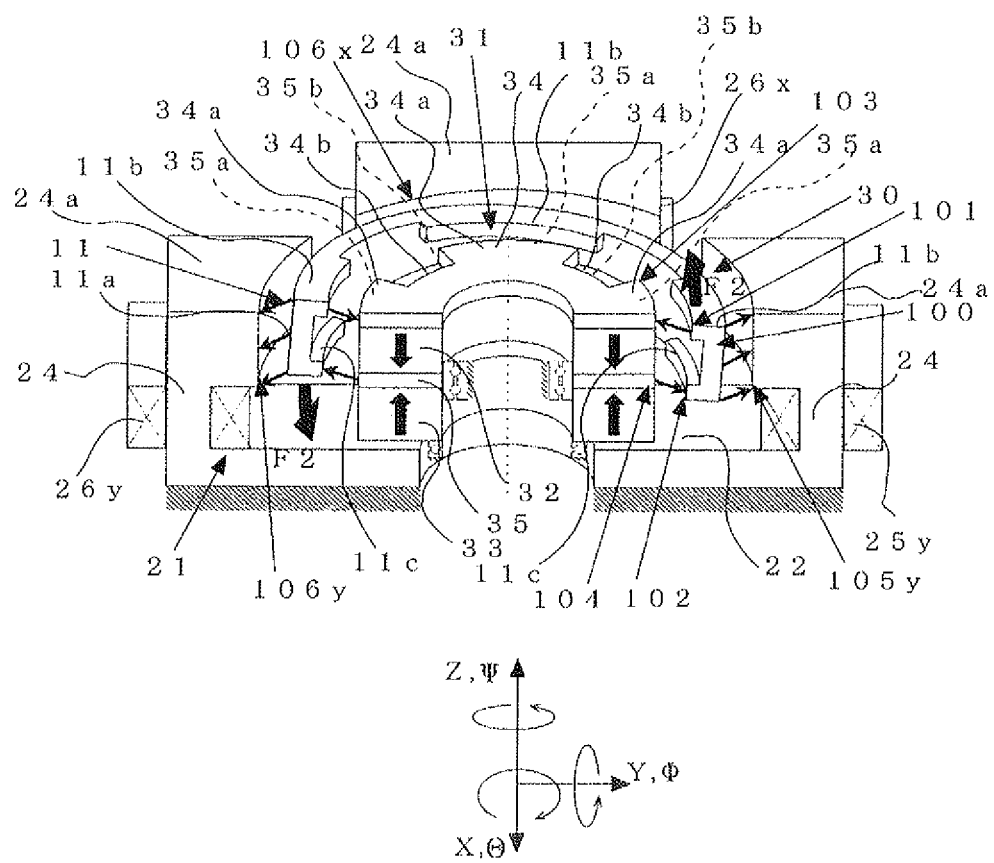
FIG. 10 is an explanation drawing showing magnetic torque F2 in the magnet bearings 30 of FIG. 1.

If angles of the ditches 34b and 35b are reduced and facing area of the protrusion sections 11b and 11c of the torque transmission disc 31 and the rotor 11 becomes large, a tendency that restoring force F1 and restoring torque F2 in an axial direction and in lean directions as shown in FIG. 9 and FIG. 10 become large is confirmed from numerical analysis. On the other hand, if the angles of the ditches 34b and 35b are too small or too large, the propagation torque as shown in FIG. 4 becomes small. Therefore, desired ditch angles to be able to achieve desired restoring force F1 and desired restoring torque F2, and desired propagation torque should be decided by using numerical analysis and others.

The depth of the ditches 34b and 35b influences mainly magnitude of the propagation torque and appropriate ditch depth should be decided by using numerical analysis and others. The number of the ditches does not necessarily have to be four, like this case. Theoretically, the restoring force F1 and the restoring torque F2 of FIG. 9 and FIG. 10 can be generated in zero or more than zero ditch, and the propagation torque of FIG. 4 can be generated in one or more than one ditch.

Next, the reason why the two permanent magnets 32 and 33 in the torque transmission disc 31 are disposed to face each other will be described.

Because it has become clear from magnetic field analysis that support rigidity in an axial direction and in lean directions of the rotor 11 becomes greater (i.e., the magnetically-levitation becomes more stable) by making the two permanent magnets 32 and 33 face each other than by using only one permanent magnet, architecture of the present embodiments has been adopted.

Even if the magnetized directions of the permanent magnets 32 and 33 do not face each other and are the same as each other, the present magnet bearings 30 can be realized. However, it becomes clear from the magnetic field analysis that the support rigidity in the axial direction and the lean directions of the rotor 11 is smaller than by making them face each other.

Theoretically, the permanent magnets do not have to be two layers; it can be realized by being three or more than three layers by an iron ring being inserted between them.

However, because architectonic constraint that height of the rotor 11 is fixed to be 10 mm has been set in the present embodiment, the case that the two neodymium permanent magnets 32 and 33 are used has been described.

If a ring component 35 inserted between the permanent magnets 32 and 33 is too small in thickness, magnetic saturation of the ring component 35 occurs and then magnetic resistance becomes large. Therefore, in the present embodiment, thickness to the extent that magnetic flux density of the ring component 35 is just barely saturated or almost saturated is obtained from the magnetic field analysis.

Therefore, it is necessary to design by paying attention to saturation of magnetic flux density in the case that the ring component 35 is thinned when three or more than three layers are adopted.

The torque transmission disc 31 is installed on the stator 21 as shown in FIGS. 6(a) to (c).

At first, as shown in FIG. 6(a), the four electro magnets 25x, 26x, 25y, and 26y for magnet bearings are arranged in the mounting section 24b of electro-magnet core 24 of the stator 21 at every 90 degrees.

Next, as shown in FIG. 6(b), the rotating shaft 28 is installed in the shaft hole 23 through bearings 29.

Then, as shown in FIG. 6(c), a spacer 36 is attached to the rotating shaft 28 protruding from the bottom plate section 22 of the electro-magnet core 24, the rotating shaft 28 is inserted into the shaft hole 31a of the torque transmission disc 31 on the spacer 36, an arrangement core 38 is installed from the shaft hole 31a of the torque transmission disc 31 by setting an opening 37 of 0.5 mm to the bottom plate section 22 of the electro-magnet core 24 and is fixed to the rotating shaft 28 with a screw 39. Although the opening 37 is here set to be 0.5 mm, it may be an opening of the extent to which it is not touched on the bottom plate section 22 of the electro-magnet core 24 when rotating the torque transmission disc 31 and it is not limited to this.

A driving shaft 42 of a motor 41 is coupled to the rotating shaft 28 through a coupling 43 so as to rotationally drive the torque transmission disc 31. A spacer 40 made from plastics is disposed between the motor 41 and the stator 21 in which torque transmission disc 31 is installed, and the driving shaft 42 of the motor 41, the coupling 43, the rotating shaft 28, and the bearings 29 are isolated by the plastic spacer 40. Note that because power supply to the motor 41 is performed by usual method, its explanation is omitted.

The first displacement sensor 44a and the second displacement sensor 44b, which measure displacement of the rotor 11 in radial directions, for example, is installed in a sensor electrode holder 44c made from synthetic resin such as polyetherimide resin and is installed between the protrusion sections 24a of the stator 21 so that the first displacement sensor 44a and the second displacement sensor 44b do not react. The first displacement sensor 44a and the second displacement sensor 44b target at outer surface of the rotor 11. Note that because power supply to the first displacement sensor 44a and the second displacement sensor 44b is performed by usual method, its explanation is omitted.

The stator 21, the torque transmission disc 31, the motor 41, the first displacement sensor 44a, and the second displacement sensor 44b are installed in a pump housing 45.

The pump housing 45, for example, comprises a doughnut-shaped top housing 45a made from duralumin and a bottom housing 45b equipped with radiating fin in lateral face. A rubber sheet 47 for water-proof and heat insulation are equipped between the top housing 45a and the bottom housing 45b.

The top housing 45a is fastened with screws to the protrusion sections 24a of the electro-magnet core 24. In the present embodiment, as shown in FIG. 2, a pump head section 10 is forced to face the torque transmission disc 31 by inserting a cylindrical rotor accommodation section 15a into a rotor insertion section 27 of a pump section 20, and a bottom section 15a' of the second housing 15 is placed on the top housing 45a of the pump section 20. The pump head section 10 is constructed so as to be fixed using friction between the pump head section 10 and the stator 21.

The bottom housing 45b, for example, fixes the motor 41 to the bottom section through a motor fixture 46 made from duralumin. In the motor fixture 46 made from duralumin, for example, a spacer 40 made from synthetic resin such as polycarbonate, which is interposed between the motor 41 and the stator 21, is placed. The heat generated by the motor 41 is transmitted to the bottom housing 45b equipped with the radiating fin in lateral face through the motor fixture 46 made from duralumin and is radiated into the atmosphere. Because the spacer 40 is made from synthetic resin, the heat generated by the motor 41 is hard to be transmitted to the electro-magnet and furthermore blood in the pump head section 10, and thus haemolysis and bloodclot formation by heating are restrained.

The pump section 20 constructed in this way comprises the rotor insertion section 27 formed by the protrusion sections 24a of the electro-magnet core 24 in extracted in lateral face of the top housing 45a. The pump section 20 forms an opening to which the cylindrical rotor accommodation section 15*a* of the pump head section 10 are inserted and extracted by the torque transmission disc 31.

Next, a control equipment 50 will be described.

In the disposable magnetically-levitated centrifugal pump 1 according to the present embodiment, the control equipment 50 is installed to compensate (1) magnetic attractive force due to magnetic fluxes 111 and 112 in X and Y directions, (2) "imbalance force due to inconsistency between rotation center and center of inertia" when rotating the rotor 11, (3) hydrodynamic force when circulating blood, and (4) various disturbance force due to impact or vibrations of when the pump 41 is tipped over and/or ambulance cars and/or others, and to perform feedback control so as to keep the rotor 11 being without contact in the X and Y directions.

The control equipment 50 comprises an input unit, which accepts measured data from the first displacement sensor 44*a* and the second displacement sensor 44*b* measuring displacement in radial (X,Y) directions on lateral face (target) of the rotor 11, an arithmetic logical unit, which calculates the displacement by comparing inputted measured-value and target position, and an electric power feed section, which supplies electronic current necessary to return the target to the target position into either of the electro-magnets 25*x*, 26*x*, 25*y*, and 26*y*.

When the electronic current is supplied into the electro-magnets 25*x*, 26*x*, 25*y*, and 26*y* by feedback control of this control equipment 50, a magnetic flux 113 is generated and the rotor 11 is displaced.

Next, a magnet bearing 30 in the present embodiment will be described.

The magnet bearings 30 are bearings that rigidity in 5 degrees of freedom except a direction of rotation ($\Psi$ direction) around a thrust direction (Z direction) of the impeller 12 is positive.

The 5 degrees of freedom comprise 1 degree of freedom in the thrust direction (the Z direction), 2 degrees of freedom in radial directions (X direction and Y direction), and 2 degrees of freedom in lean directions ($\Theta$ direction and $\Phi$ direction), and the thrust direction corresponds to a rotating shaft direction of an impeller 9, the radial directions correspond to directions perpendicular to the rotating shaft direction, and the lean directions correspond to directions of small rotation around the radial directions.

In a case, sign of rigidity of virtual magnetic coupling becomes positive with respect to 3 degrees of freedom comprising the thrust direction (the Z direction) and the lean directions (the $\Theta$ direction and the $\Phi$ direction). In other words, when the rotor 11 is displaced in 1 degree of freedom in the thrust direction (the Z direction) from the ideal position as shown in FIG. 9, the restoring force F1 due to loop of the magnetic flux 111 operates on the rotor 11.

In addition, as shown in FIG. 10, when the rotor 11 inclines in 2 degrees of freedom in the lean directions from ideal position, the restoring torque F2 due to loop of the magnetic fluxes 111 and 112 operates on the rotor 11.

Figure 7:
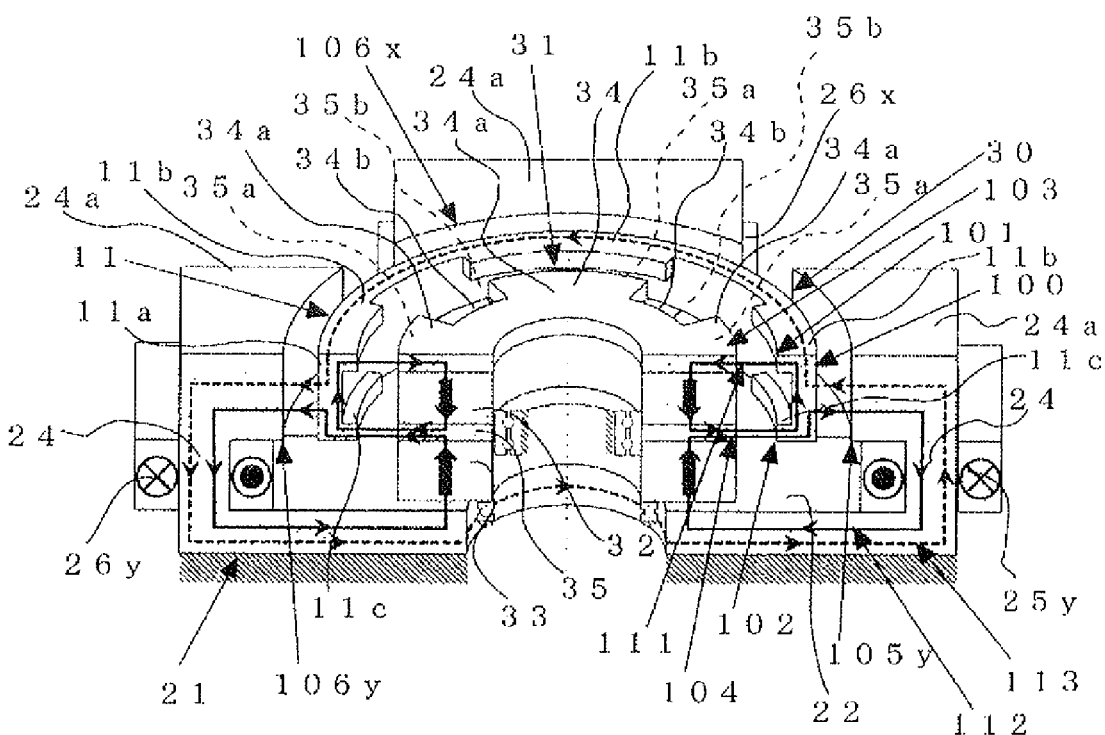
FIG. 7 is an explanation drawing showing a magnetic circuit in the magnet bearings 30 of FIG. 1.
Figure 7:
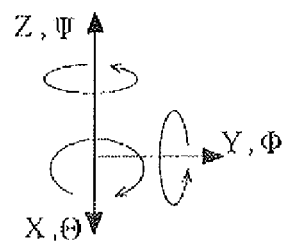

In either case, as shown in FIG. 7, the rotor 11 moves toward a state (i.e., an aligned state at ideal position), in which a pole-face 101 faces a pole-face 103 of the torque transmission disc 31, a pole-face 102 faces a pole-face 104 of the torque transmission disc 31, and a pole-face 100 faces pole-faces 105*y* and 106*y* of electro-magnet 25*y*, by the restoring force F1 or the restoring torque F2.

As a result, the rotor 11 is held in the aligned state that respective of the pole-faces 101 and 102 faces the pole-faces 102 and 103 and the pole-face 100 faces the pole-faces 105*x*, 106*x*, 105*y*, and 106*y*. In other words, with respect to 3 degrees of freedom in the non-control directions that comprise the thrust direction and the lean directions, rigidity of the rotor 11 can be ensured enough by loops of the magnetic fluxes 111 and 112 from the permanent magnets 32 and 33.

In contrast, with respect to 2 degrees of freedom in the radial directions, virtual spring rigidity due to loop of the magnetic fluxes 111 and 112 from the permanent magnet 32 and 33 results in "negative".

Therefore, in the present embodiment, for the purpose to compensate rigidity of magnetic coupling in the radial directions and to make it "positive", magnetic excitation current is supplied to each coil of the electro-magnets 25*x*, 25*y*, 26*x*, and 26*y* for X- and Y-directional control by the control equipment 50. In addition, direction and intensity of the magnetic excitation current for each coil are feedback-controlled based on output signal from the first displacement sensor 44*a* and the second displacement sensor 44*b*.

Figure 5:
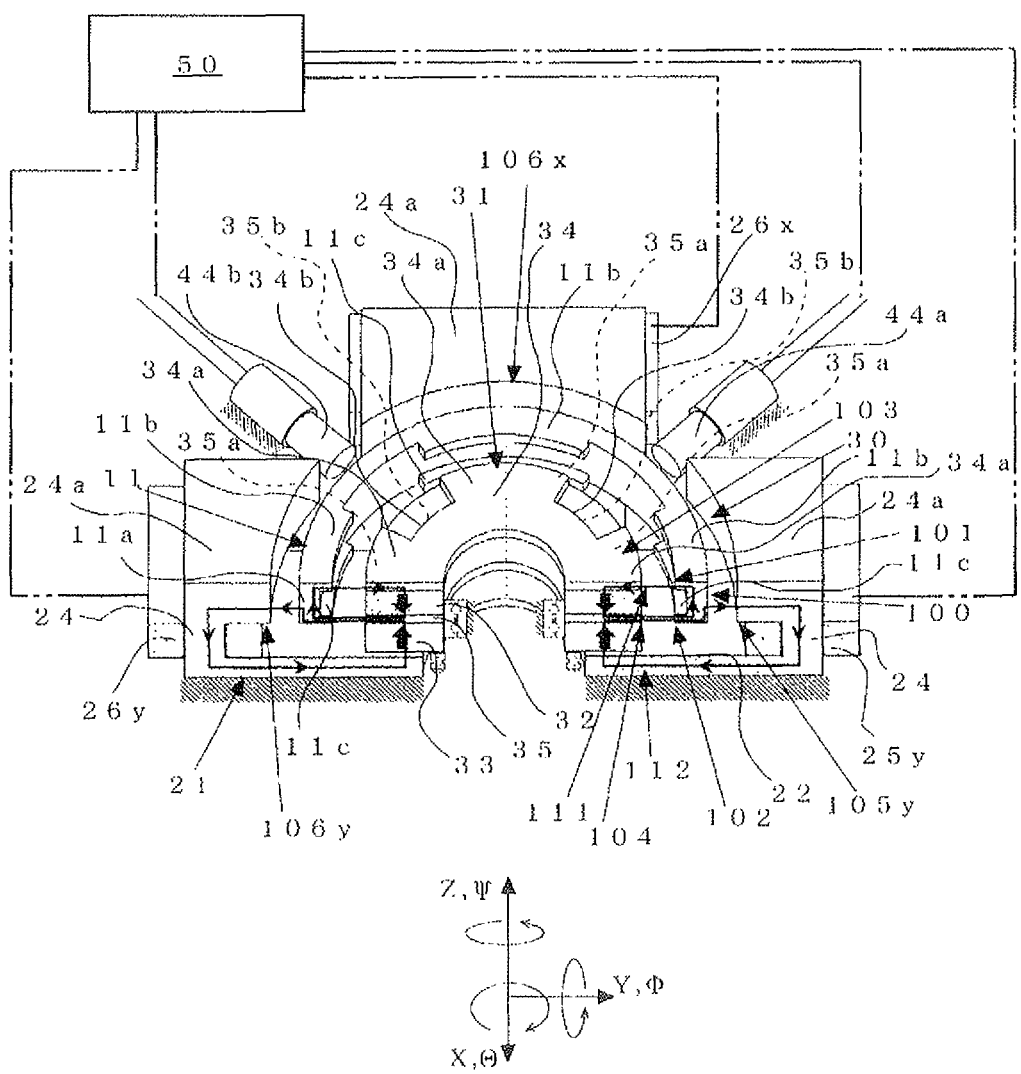
FIG. 5 is an explanation drawing showing a magnetic circuit in the magnet bearings 30 of FIG. 1.
Figure 6:
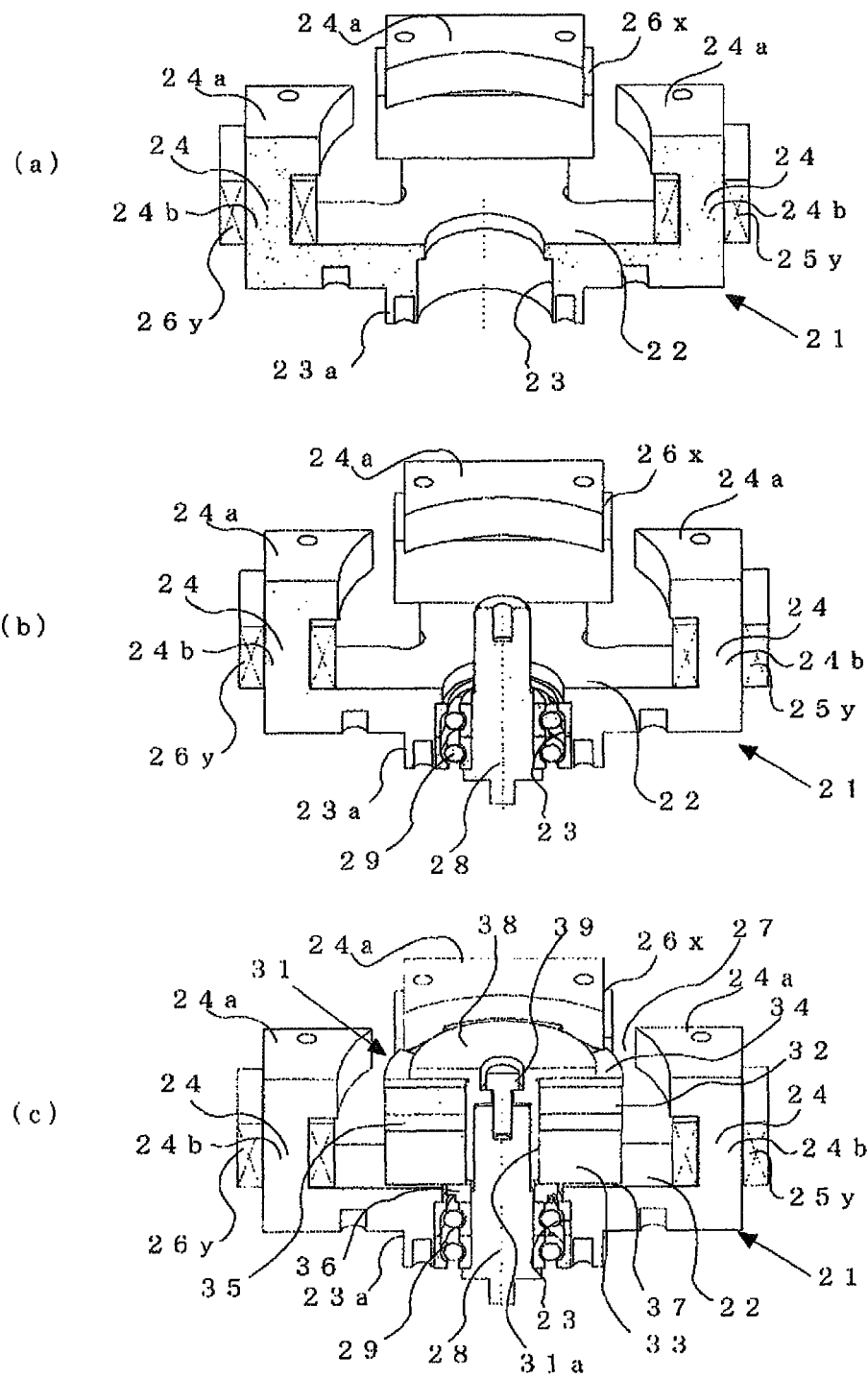
FIG. 6 is an explanation drawing showing installation of the torque transmission disc 31 to the stator 21 of FIG. 1.

As shown in FIG. 3 and FIG. 5, because the first displacement sensor 44*a* and the second displacement sensor 44*b* are spaced at 90 degrees between the protrusion sections 24*a* of the electro-magnets 25*x*, 26*y*, 25*x*, and 25*y*, and are installed using a sensor fixture 44*c* so that the first displacement sensor 44*a* and the second displacement sensor 44*b* face toward the center of the rotor 11, in these first displacement sensor 44*a* and second displacement sensor 44*b* displacement of the rotor 11 in the radial directions, specifically displacement of the pole-face 100 of circumference lateral face of the rotor 11 can be measured.

The control equipment 50, as described above, is composed to be feedback-controlled so that the rotor 11 returns to the target position by comparing output signals from the first displacement sensor 44*a* and the second displacement sensor 44*b* and a target position signal of the rotor 11 in the radial directions.

For example, not shown here, but when the rotor 11 is displaced from an ideal position in 1 degree of freedom in the Y direction, in order to generate controlling force in reverse direction to the displacement direction, the control equipment 50 feedback-controls direction and intensity of magnetic excitation current to supply into coils of electro-magnets 25*y* and 26*y* for Y direction control.

Figure 11:
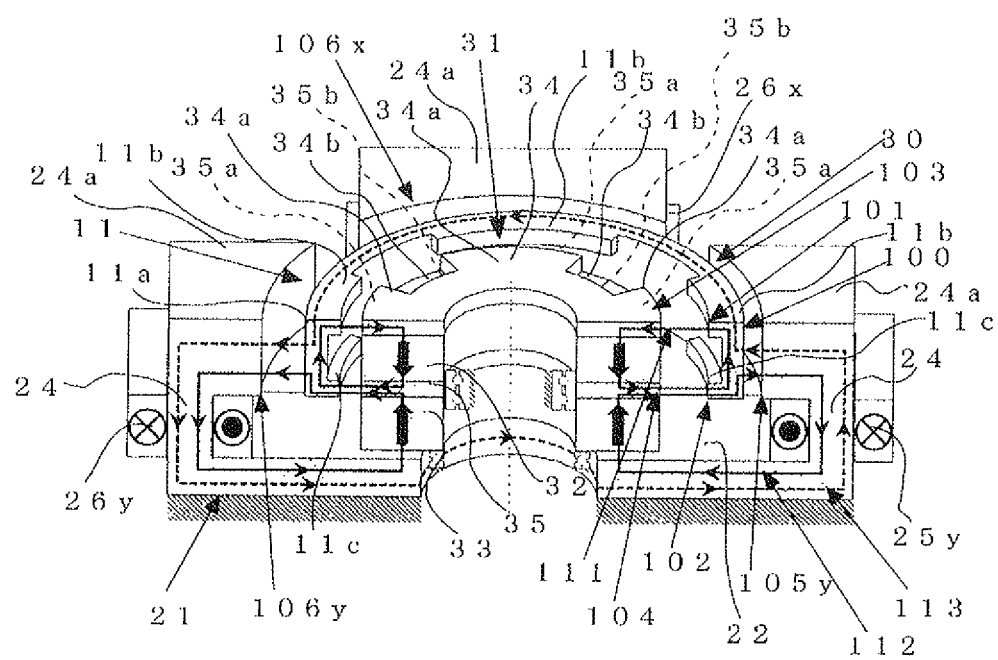
FIG. 11 is an explanation drawing showing feedback control by control equipment when the rotor 11 of FIG. 1 is displaced towards a pole-face 105y.
Figure 11:
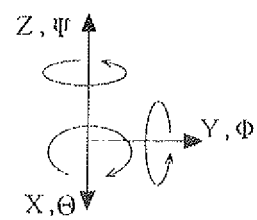

Therefore, as shown in FIG. 11, if the rotor 11 is displaced towards the pole-face 105*y*, the magnetic flux 113, which is opposite in direction to the magnetic flux 112 on the side of the pole-face 105*y* and is equal in direction to the magnetic flux 112 on the side of the pole-face 106*y*, is generated by electro-magnets. Then, the magnetic flux 112 is weakened in the magnetic circuit via the side of the pole-face 106*y*, and the magnetic flux 112 is strengthened in the magnetic circuit via the side of the pole-face 106*y*.

As a result, controlling force that pulls back the rotor 11 to the side of the pole-face 106*y* is generated.

Therefore, the rotor 11 is stably held at a target position in which a gap on the side of the pole-face 105*y* is the same as a gap on the side of the pole-face 106*y*.

In addition, also in displacement of the rotor 11 in the X direction, similar feedback control is performed with respect to the protrusion sections 24*a* of the electro-magnets 25*x* and 26*x* including the pole-faces 105*x* and 106*x* and coils wound up there, the rotor 11 is stably held at a target position in which the gap on the side of the pole-face 105*x* of the electro-magnets 25*x* and 26*x* is the same as the gap on the side of the pole-face 106*x*.

In other words, with respect to 2 degrees of freedom in the radial directions, virtual spring rigidity becomes "positive" by composition of loops of the magnetic fluxes 111 and 112 from the permanent magnets 32 and 33 with loops of the magnetic flux 113 from the electro-magnets 25x, 26x, 25y, and 26y, and as a result, enough rigidity of the rotor 11 can be ensured.

In this way, in the magnet bearings 30 of the present embodiment, with respect to 3 degrees of freedom in non-control directions comprising a thrust direction and lean directions of the rotor enough rigidity can be ensured by loops of the magnetic fluxes 111 and 112 from the permanent magnets 32 and 33, and furthermore with respect to 2 degrees of freedom in the radial directions, enough rigidity can be ensured by composition with loop of the magnetic flux 113 from the electro-magnet. In other words, high rigidity in 5 degrees of freedom is realized.

Next, effect of the disposable magnetically-levitated centrifugal pump 1 according to the present embodiment will be described.

At first, as shown in FIG. 2, not only the pump head section 10 is forced to face the torque transmission disc 31 by inserting the cylindrical rotor accommodation section 15a into the rotor insertion section 27 of the pump section 20, but also the bottom section of the second housing 15 is placed on the top housing 45a of the pump section 20.

Next, by magnetic coupling occurring between the rotor 11 and the torque transmission disc 31 and by magnetic coupling occurring between the electro-magnets 25x, 26x, 25y, and 26y and the rotor 11, the rotor 11 and the impeller 12 are magnetically raised to be in a state of complete non-contact with respect to the pump head housing 13 and is supported in the non-contact state.

Then, the motor 41 is rotationally driven in this state, and, as shown in FIG. 4, when the torque transmission disc 31 is rotated towards an arrow direction (Ψ direction), torque is transmitted to the rotor 11 by magnetic coupling occurring between the torque transmission disc 31 and the rotor 11, and the rotor 11 rotates in the same direction, and then the impeller 12 rotates in the same direction.

Therefore, blood flowing in from a blood flow inlet 14a of the top section of the pump head housing 13 is given kinetic energy by rotation of the impeller 12 and flows out from a blood flow outlet 14b in lateral face. Then, as stated above, at the time of rotation of this impeller 12, because the magnet bearings 30 restore displacement and lean in a thrust direction (Z direction) and lean directions (Θ direction and Φ direction) of the rotor 11 to an ideal position and displacement of radial directions (X direction and Y direction) is feedback-controlled through the magnet bearings 30 by the control equipment 50 and the rotor 11 is restored to an ideal position, the rotor 11 and the impeller 12 are stably rotated in the Ψ direction.

In addition, with driving of the motor 41, the motor 41 is heated by copper loss and iron loss due to variation of magnetic field, as stated above, in the present embodiment, the generated heat of the motor 41 is transmitted to the bottom housing 45b provided with a radiating fin on lateral face through the motor fixture 46 made from duralumin and is radiated in the atmosphere. Because the spacer 40 is made from synthetic resin, the generated heat of the motor 41 is hard to be transmitted to the electro-magnets and furthermore blood of the pump head section 10, and as a result haemolysis and bloodclot formation by heating are restrained. Besides, because the torque transmission disc 31 rotates synchronously with the rotor 11, variation of magnetic field does not occur near the pump head housing 13.

Then, if a blood contact section consisting of the pump head housing 13 and the rotor 11 and/or the impeller 12 installed inside of this is replaced, a new pump head section 10 may be installed in the pump section 20 after removing the pump head section 10 from the pump section 20.

In this way, the disposable magnetically-levitated centrifugal pump 1 according to the present embodiment has the advantages that durability is improved as compared with conventional examples, in which an impeller is supported with contact-type bearings because of the structure supporting the impeller 12, which is incorporated within the pump head section 10, without contact at the magnet bearings 30, expiration date of the disposable section can be extended drastically, and furthermore malfunction in the conventional examples such as thrombus around the bearings and haemolysis due to the bearings can be eliminated.

In addition, in the present embodiment, not only the motor 41 is estranged from the pump head section 10 and is disposed in the footing of the stator 21, but also the rotating shaft 28 for power transmission is made from material having low thermal conductivity and heat of the motor 41 is hard to be transmitted to blood flowing down in the pump head section 10, and as a result, blood coagulation caused by heat can be surely prevented.

Furthermore, as stated above, if electromagnetic soft iron cores of the electro-magnets 25x, 26x, 25y, and 26y are made from pure iron formed by annealing process, hysteresis-loss of the magnet bearing 30 decreases, and it contributes to low heat generation of the electro-magnets 25x, 26x, 25y, and 26y, and as a result, coagulation of blood flowing down within the pump head 10 can be prevented. In addition, if electromagnetic soft iron cores are made from powder core, eddy-current loss decreases, and then not only it contributes to low heat generation of the electro-magnets 25x, 26x, 25y, 26y, but also band width of electro-magnetic force to control lift-off from the magnet bearing 30 can be extended, and as a result there is an advantage that vibration of the rotor 11 is reduced and it contributes to haemolysis prevention and/or prevention of blood coagulation.

In addition, magnetic reluctance of magnetic circuit is also small and thus it is also advantageous for reducing the power consumption of the magnet bearing.

Furthermore, the present embodiment has an advantage that because neodymium permanent magnet is not used for the rotor 11 in the pump head section 10 which is a disposable section. it can contribute to price reduction of the disposable section by realizing simple rotor structure, compared to examples of the patent document 1 and the non-patent documents 1~3.

In addition, according to the present embodiment, because falling prevention of the disposable pump head section 10 is designed by using friction between outer circumference surface of bottom section of the pump head section 10 and internal circumference surface of the top housing 45a of the pump section 20, unexpected situation that the pump head section 10 falls off when using it during and after cardiac surgery does never occur.

As mentioned above, according to the present embodiment, the magnetically-levitated centrifugal pump, which can float impeller, has been able to be realized without using permanent magnet for the rotor 11, without changing rigidity of support, force to support, and torque to rotate with magnetic coupling, and without changing diameter, internal diameter, and gap of the impeller in the pump of the patent reference 1.

In addition, according to the present embodiment, because permanent magnet is not used in the rotor 11 including the impeller 12 at all and only one component of the magnetic material (e.g., pure iron) is used, the number of the components decreases. Because expensive neodymium permanent magnet is not used, reduction in cost can be realized.

In addition, although in neodymium permanent magnet there is difficulty in processing, because in the present embodiment the rotor 11 is consisted of iron, which is easy to process, and the others and component shape is a simple structure that one ditch and four ditches are respectively processed along hoop direction for internal circumference of the ring-shaped rotor body 11a and along axial direction, accuracy of processing is improved. As a result, rotational accuracy of the rotor 11 is improved.

In addition, because neodymium permanent magnet is not used in the rotor 11, there is an advantage that the rotor 11 and the impeller 12 are able to be integrated by injection molding and the pump head 10 which is disposable component can be produced at low cost. In contrast, when neodymium permanent magnet is used for the rotor, as given in the patent reference 1, it has been difficult to integrate by being embedded the impeller when injection molding because demagnetization temperature of neodymium permanent magnet is low. Therefore the conventional impeller was not integrated with a rotor by injection molding. Thus there was a disadvantage that disposable components become expensive.

Furthermore, to make the rotor 11 magnetically-levitated and to make the rotor 11 rotate by transmitting from an external motor 41 to torque, shape and constituent of electromagnets for magnet bearings and torque transmission disc, which does not exist in the conventional magnetically-levitated centrifugal pump, can be suggested.

Shown in Table 1 is a comparison of support rigidity in axial direction and support rigidity in lean direction in the disposable magnetically-levitated centrifugal pump 1 according to the present embodiment and the disposable magnetically-levitated centrifugal pump described in the patent reference 1.

Here, properties of materials are as follows.

Permanent magnet is neodymium permanent magnet of residual magnetic flux density of 1.2 T, and coercive-force of 890 kA/m.

In magnetic material components (the rotor 11, the electromagnet core, and the ring component of magnetic coupling), pure iron (or materials having the same magnetic characteristic as the pure iron) was applied to magnetic field analysis.

Figure 12:
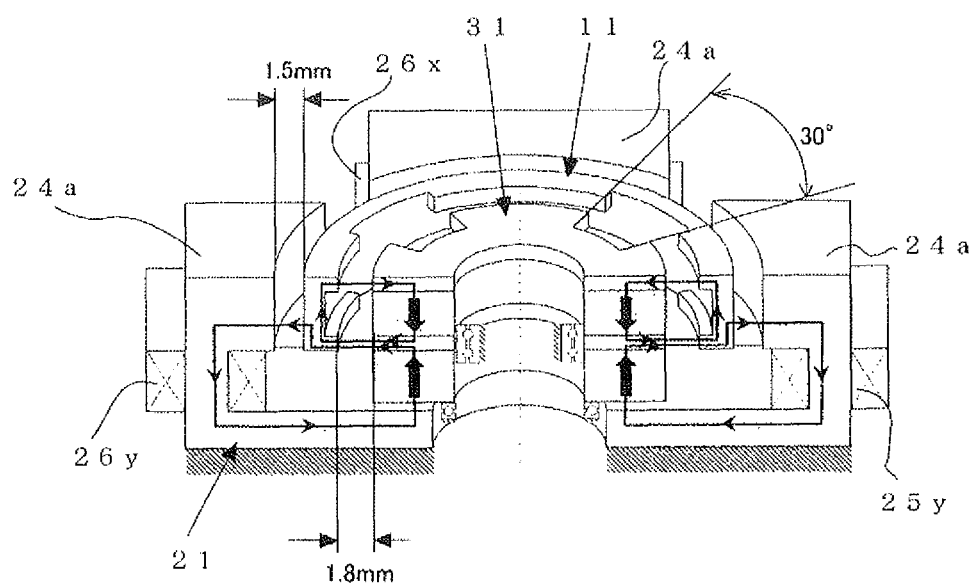
FIG. 12 is an explanation drawing that indicates a gap between the rotor 11 of the magnetically-levitated blood pump 1 of FIG. 1 and each of electro-magnets 25x, 26x, 25y, and 26y, a gap between the rotor 11 and the torque transmission disc 31, and an angle of a tooth space in the rotor 11 and the torque transmission disc 31, when the disposable magnetically-levitated centrifugal pump 1 of FIG. 1 is compared with the disposable magnetically-levitated centrifugal pump of the patent reference 1.
Figure 12:
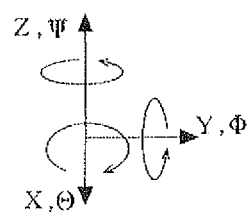

In addition, dimension that is thought to influence significantly magnetic properties is shown in FIG. 12.

Gap between the rotor 11 and each of the electro-magnets 25x, 26x, 25y, and 26y for magnet bearing is 1.5 mm.

Gap between the rotor 11 and the torque transmission disc 31 is 1.8 mm.

Angular degree of tooth space of the rotor 11 and the torque transmission disc 31 is 30 degrees.

TABLE 1

| | The present embodiment | Patent reference 1 Magnets exist. | Patent reference 1 No magnet exists. |
|---|---|---|---|
| Rigidity in axial direction | 56 N/mm | 52 N/mm | 2.5 N/mm |
| Rigidity in lean direction | 8.4 Nm/rad | 9.0 Nm/rad | 0.8 Nm/rad |

As is clear from Table 1, according to the disposable magnetically-levitated centrifugal pump 1 of the present embodiment, though permanent magnet was not used for the rotor 11, support rigidity in the axial direction and rigidity in the lean direction were 10~20 times as much as the disposable magnetically-levitated centrifugal pump without magnets as described in the patent reference 1 and were equal to the disposable magnetically-levitated centrifugal pump with magnets as described in the patent reference 1.

Next, the disposable magnetically-levitated centrifugal pump 1 according to the present embodiment and the disposable magnetically-levitated centrifugal pump without magnets as described in FIG. 8 of the patent reference 1 will be described by comparing them.

Figure 8:
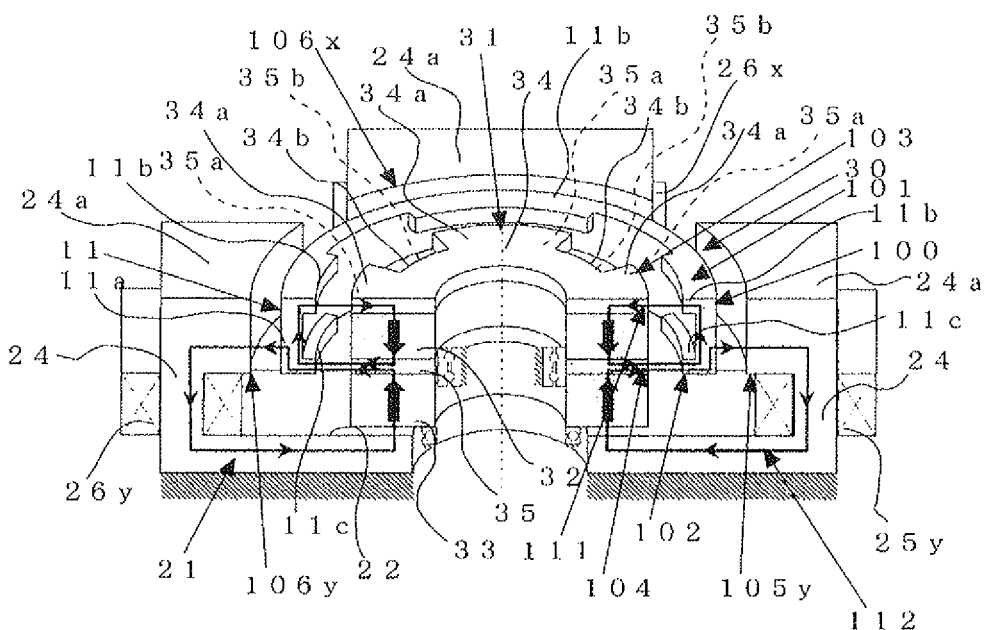
FIG. 8 is an explanation drawing showing a magnetic circuit with the neodymium permanent magnet in the magnet bearings 30 of FIG. 1.
Figure 8:
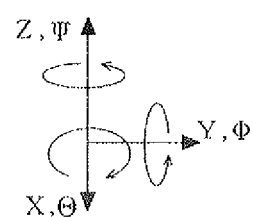
Figure 13:
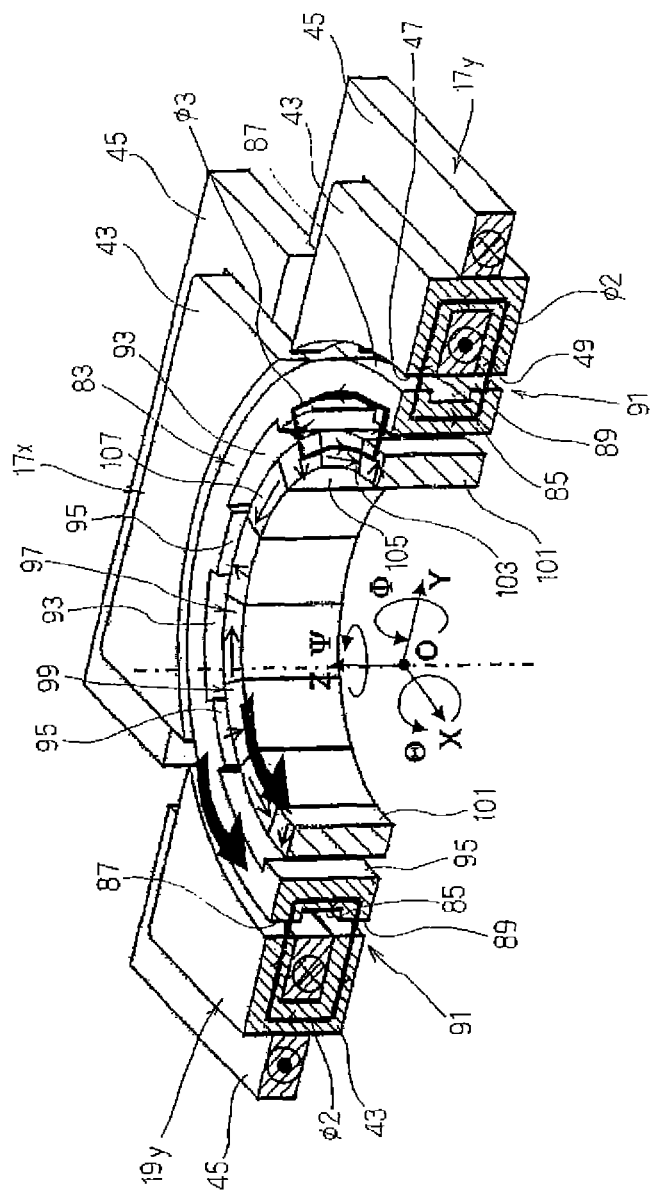
FIG. 13 is an apparatus disclosed in the prior art.

As also shown in FIG. 8 of WO 2007/029623 A1 (the patent reference 1), which is depicted as FIG. 13 herein, magnet bearing consisting of only magnetic material ring without using permanent magnet for the rotor is described. Common point between the disposable magnetically-levitated centrifugal pump 1 according to the present embodiment and the disposable magnetically-levitated centrifugal pump without magnets as described in FIG. 8 of WO 2007/029623 A1 (the patent reference 1), which is depicted as FIG. 13 herein, is that only magnetic material is used for the rotor, and different point between them is that the disposable magnetically-levitated centrifugal pump 1 according to the present embodiment has a shape providing higher rigidity. In the present embodiment, rigidity of around 20 times in comparison with the disposable magnetically-levitated centrifugal pump described in FIG. 8 of WO 2007/029623 A1 the patent reference 1), which is depicted as FIG. 13 herein, is provided.

As mentioned above, there is a problem that fabrication is difficult because small fan-shaped magnets are arranged on periphery in the torque transmission disc of the disposable magnetically-levitated centrifugal pump without magnet as described in FIG. 8 of the patent reference 1.

In contrast, in the disposable magnetically-levitated centrifugal pump 1 according to the present embodiment, fabrication is very simple because the torque transmission disc 31 has a shape that the cylindrical permanent magnets 32 and 33 and the ring components 34 and 35 of magnetic materials are only piled Next, the reason why difference in rigidity between the disposable magnetically-levitated centrifugal pump 1 according to the present embodiment and the disposable magnetically-levitated centrifugal pump without magnet as described in FIG. 8 of WO 2007/029623 A1 (the patent reference 1), which is depicted as FIG. 13 herein, occurred will be examined.

This is thought to be that because dimensions of permanent magnets of the torque transmission disc are different from each other, the present embodiment has larger magnetomotive force, in other words, magnetic flux density of magnetic circuit of the present embodiment became larger. It height of the rotor is fixed to be 10 mm, as shown in FIG. 8 of WO 2007/029623 A1 (the patent reference 1), which is depicted as FIG. 13 herein, height of the magnet used for the torque transmission disc can be raised only up to around 10 mm. If the magnet of the torque transmission disc becomes higher than the rotor, like 15 mm and 20 mm, restoring force in the Z direction to put back does not occur enough when the rotor was displaced to the Z direction.

In contrast, in the present embodiment, for example, as shown in FIG. 7, for the rotor 11 of 10 mm in height, there is a height limit in the permanent magnet 32, similar to FIG. 8 of WO 2007/029623 A1 (the patent reference 1), which is depicted as FIG. 13 herein, height of the permanent magnet 33 is permissible to be raised as much as one likes. To describe in an extreme manner, if height of the permanent magnet 33 is raised until magnetic saturation of magnetic material occurs and its volume is enlarged, strong magnetic circuit is provided. In the present embodiment, because depth from top edge of the protrusion sections 24*a* forming the rotor insertion section 27 to the bottom plate section 22 becomes greater than protrusion length of the rotor accommodation section 15*a*, enough height of the permanent magnet 33 can be achieved.

In addition, although the case that the four electro-magnets 25*x*, 26*x*, 25*y*, and 26*y* for magnet bearings are installed in the stator 21 is explained in the embodiment mentioned above, the present invention is not limited to this case and the number is arbitrary while magnetic circuit can be formed. For example, even if the number of the electro-magnets for magnet bearing is both three or live, the electro-magnets are arranged on the circumference of the rotor 11 at even intervals, displacements in the X direction and the Y direction of the rotor 11 are calculated with the first displacement sensor 44*a* and the second displacement sensor 44*b*, forces in the X direction and in the Y direction that are necessary for magnetically-levitation are calculated with control equipment, and then by supplying current that is appropriate in each electro-magnet so that the calculated forces in the X direction and the Y direction are generated, the rigidity in the X and Y directions can be made "positive".

In addition, in the embodiment mentioned above, although the electro-magnet core 24 is explained as being the one that four mounting sections 24*b* are installed to substantially cross-shaped bottom plate section 22, the present invention is not limited only to this and shape of the bottom plate section 22 is arbitrary.

In addition, in the embodiment mentioned above, although the case that the respective four electro-magnets 25*x*, 26*x*, 25*y*, and 26*y* for magnet bearing is installed by winding coils around the four mounting sections 24*b* of the electro-magnet core 24 is explained, the present invention is not limited only to this and they may be installed on the protrusion sections 24*a* of the electro-magnet core 24 or the bottom plate section 22.

In addition, in the embodiment mentioned above, although the case that the present invention is applied to the disposable magnetically-levitated centrifugal pump is explained, the present invention is not limited only to this and, for example, it is possible to apply to the magnetically-levitated centrifugal pump using and throwing away the impeller section such as a canned pump.

The invention claimed is:

1. A disposable magnetically-levitated centrifugal pump comprising a pump head section and a pump section, characterized in that, the pump head section which comprises:
   a cylindrical rotor, which is made from magnetic material and has a ring-shaped rotor body, the cylindrical rotor having rotor protrusions at upper part and at lower part of internal circumference surface of the ring-shaped rotor body, the protrusions having specified width and protruding toward an inside direction of the ring-shaped rotor body;
   an impeller which rotates accompanying with rotation of the cylindrical rotor; and
   a pump head housing which comprises:
      a fluid inlet;
      a fluid outlet;
      a space section in which the impeller is configured to rotate freely; and
      a rotor accommodation section in which the cylindrical rotor is accommodated and is configured to rotate freely by means of magnetic force, the rotor accommodation section being configured to protrude from a bottom surface of the space section, wherein the pump section comprises:
   a stator which has:
      a rotor insert section on the side of one end section, the rotor insert section having a depth larger than protrusion length of the rotor accommodation section and accommodating the rotor accommodation section in a manner that the rotor accommodation section is inserted in and removed from; a torque transmission disc which is formed by bonding ring components, which are made from material having low magnetic resistivity and comprise protrusion sections located facing the rotor protrusions, bonding one ring component between an upper ring shaped permanent magnet and a lower ring shaped permanent magnet,
      which are magnetized in a thickness direction thereof, such that like-poles face each other, and placing another ring component on top of the upper ring-shaped permanent magnet, the torque transmission disc being disposed inside the rotor insert section and being configured to magnetically couple with the rotor;
   a motor which is coupled to a rotating shaft inserted from the side of another end section of the stator to the side of the one end section, and which drives the torque transmission disc;
   a displacement sensor which is disposed on the stator and measures displacement in radial directions of the rotor; and
   a pump housing which comprises the stator, the torque transmission disc, the motor and the displacement sensor, the pump housing being able to accommodate the pump head section in a manner that the pump head section is inserted to and removed from,
wherein the stator further comprises an electro-magnet core which has a bottom plate section having a shaft hole going through the rotating shaft at the center, mounting sections which rise parallel to and in the same direction as the rotating shaft from end points of the bottom plate section, and one or a plurality of stator protrusion sections which protrude toward the central axis of the shaft hole on the upper part side of the mounting section, wherein the electro-magnet core is configured to magnetically couple with the lower ring shaped permanent magnet,
wherein the electromagnets for magnet bearings are formed by winding a coil around the electro-magnet core, and
wherein the torque transmission disc is fixed on the rotating shaft so that the upper ring-shaped permanent magnet is disposed against the rotor in the rotor insertion section and the upper ring-shaped permanent magnet and the lower ring-shaped permanent magnet are at a position between a top of the stator protrusions sections and the bottom plate section,
   wherein the bottom plate section, the mounting sections and the stator protrusion section are made from magnetic material,
   wherein the magnetic flux from the electro-magnet core enters the lower ring shaped permanent magnet from the bottom section of the lower ring shaped permanent magnet through the bottom plate section of the electro-magnet core.

2. The disposable magnetically-levitated centrifugal pump in accordance with claim 1,
   wherein the rotor and the impeller are integrated by injection molding.

3. The disposable magnetically-levitated centrifugal pump in accordance with claim 1, wherein the bottom plate section and the mounting sections are integrated.

4. The disposable magnetically-levitated centrifugal pump in accordance with claim 1, wherein the electro-magnetic core contains four core sections.

\* \* \* \* \*